(12) United States Patent
Park et al.

(10) Patent No.: US 11,883,649 B2
(45) Date of Patent: Jan. 30, 2024

(54) MINIMALLY INVASIVE ELECTRODE AND DELIVERY DEVICE AND RELATED SYSTEMS AND METHODS

(71) Applicant: NeuroOne Medical Technologies Corporation, Eden Prairie, MN (US)

(72) Inventors: Michael C. Park, Excelsior, MN (US); Mark A. Christianson, Eden Prairie, MN (US); Timothy J. Kesti, Otsego, MN (US)

(73) Assignee: NeuroOne Medical Technologies Corporation, Eden Prairie, MN (US)

( * ) Notice: Subject to any disclaimer, the term of this patent is extended or adjusted under 35 U.S.C. 154(b) by 252 days.

(21) Appl. No.: 16/911,267

(22) Filed: Jun. 24, 2020

(65) Prior Publication Data
US 2020/0398047 A1 Dec. 24, 2020

Related U.S. Application Data

(60) Provisional application No. 62/865,701, filed on Jun. 24, 2019.

(51) Int. Cl.
*A61N 1/05* (2006.01)
(52) U.S. Cl.
CPC .................................. *A61N 1/0531* (2013.01)
(58) Field of Classification Search
CPC .................................................. A61N 1/0531
See application file for complete search history.

(56) References Cited

U.S. PATENT DOCUMENTS

| | | | |
|---|---|---|---|
| 3,324,855 A | 6/1967 | Heimlich | |
| 4,158,916 A | 6/1979 | Adler | |
| 4,946,457 A * | 8/1990 | Elliott | A61N 1/3956 606/1 |
| 5,904,711 A * | 5/1999 | Flom | A61N 1/05 607/129 |
| 6,415,187 B1 * | 7/2002 | Kuzma | A61N 1/0558 607/116 |
| 7,611,455 B2 | 11/2009 | Borst et al. | |
| 8,021,362 B2 * | 9/2011 | Deem | A61B 18/1492 606/41 |
| 9,480,525 B2 * | 11/2016 | Lopes | A61B 5/6858 |
| 2003/0065364 A1 * | 4/2003 | Wellman | A61B 18/1482 607/5 |
| 2003/0124484 A1 | 7/2003 | Reiz | |

(Continued)

OTHER PUBLICATIONS

EP Pat. App. No. 20833024.1, Extended European Search Report dated May 24, 2023, 7 pages.

*Primary Examiner* — Eric D. Bertram
(74) *Attorney, Agent, or Firm* — Fredrikson & Byron, P.A.

(57) ABSTRACT

Disclosed herein are a minimally invasive electrode and delivery device, along with various related components, devices, methods, and technologies. The delivery device comprises a proximal elongate shaft, a paddle coupled to a distal end of the proximal shaft, and an irrigation/suction sleeve disposable over the paddle. Disclosed also is a fan-like cortical electrode device comprising at least two electrode segments, wherein each of the at least two electrode segments comprises a thin film pad, a plurality of electrode contacts disposed on the thin film pad, and a proximal connector attached to a proximal end of the thin film pad.

17 Claims, 14 Drawing Sheets

(56) References Cited

U.S. PATENT DOCUMENTS

| | | | |
|---|---|---|---|
| 2004/0186543 A1* | 9/2004 | King | A61M 5/14276 |
| | | | 607/116 |
| 2005/0261673 A1 | 11/2005 | Bonner et al. | |
| 2006/0129203 A1 | 6/2006 | Garabedian et al. | |
| 2008/0312716 A1 | 12/2008 | Russell | |
| 2011/0077660 A1* | 3/2011 | Janik | A61N 1/0553 |
| | | | 607/116 |
| 2015/0094734 A1* | 4/2015 | Staunton | A61N 1/0551 |
| | | | 606/129 |
| 2018/0289949 A1 | 10/2018 | Bachinski et al. | |

* cited by examiner

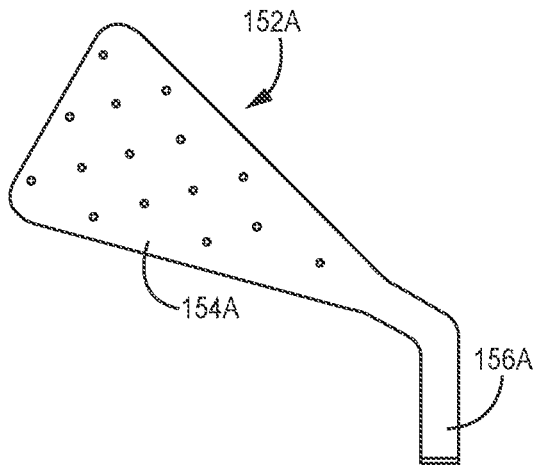
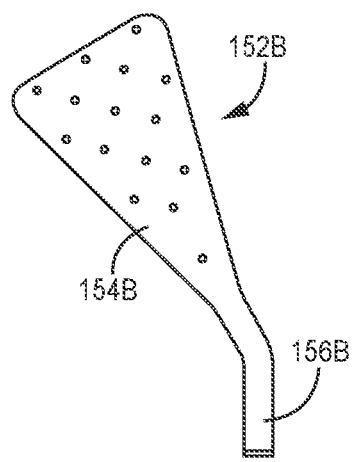
FIG. 12A    FIG. 12B
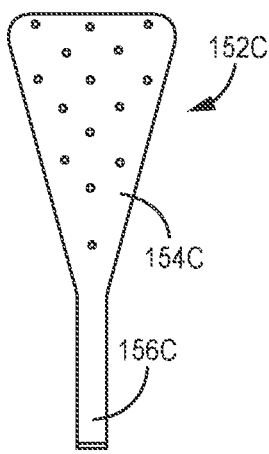
FIG. 12C
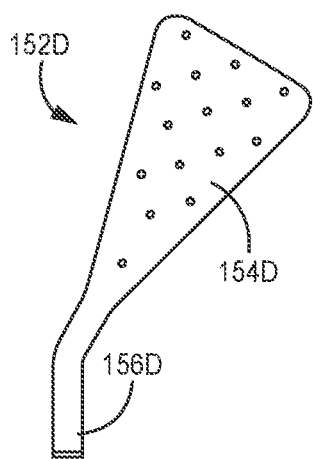
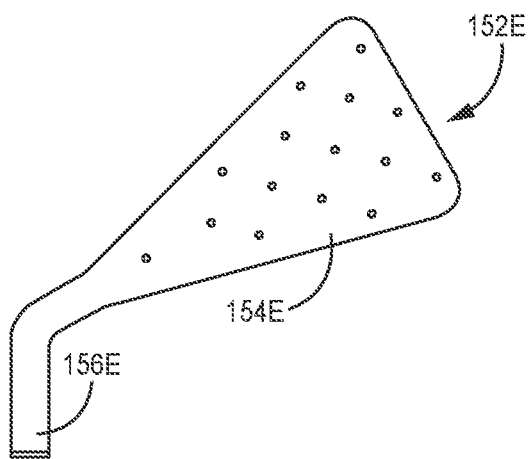
FIG. 12D    FIG. 12E

MINIMALLY INVASIVE ELECTRODE AND DELIVERY DEVICE AND RELATED SYSTEMS AND METHODS

CROSS-REFERENCE TO RELATED APPLICATION(S)

This application claims the benefit under 35 U.S.C. § 119(e) to U.S. Provisional Application 62/865,701, filed Jun. 24, 2019 and entitled "Minimally Invasive Electrode and Delivery Device and Related Systems and Methods," which is hereby incorporated herein by reference in its entirety.

FIELD

The various embodiments herein relate to neural probes and related delivery systems and methods, and more specifically to cortical probes and related delivery systems and methods.

BACKGROUND

Existing brain mapping and/or stimulation devices and procedures using electrodes are highly invasive and complex. There is a need in the art for improved, minimally invasive electrode delivery devices and related electrode devices, delivery methods, and technologies.

BRIEF SUMMARY

Discussed herein are various embodiments of an electrode delivery system, including delivery devices, electrodes (including cortical electrodes), and other related devices, methods, and technologies.

In Example 1, an electrode delivery device comprises a proximal elongate shaft defining a shaft lumen and a paddle coupled to a distal end of the proximal shaft. The paddle comprises a paddle lumen defined within the paddle and a plurality of holes defined in the paddle, wherein each of the plurality of holes is in fluidic communication with the paddle lumen and an area external to the paddle lumen. Further, the device also comprises an irrigation/suction sleeve disposable over the paddle, the irrigation/suction sleeve comprising a sleeve lumen defined within the sleeve and a plurality of holes defined in the sleeve, wherein each of the plurality of holes is in fluidic communication with the sleeve lumen and an area external to the sleeve lumen. In addition, the tube lumen, the paddle lumen, and the sleeve lumen are in fluidic communication.

Example 2 relates to the electrode delivery device according to Example 1, wherein the paddle has a length substantially equal to a length of the sleeve lumen such that a combination of the paddle and the irrigation/suction sleeve is relatively rigid.

Example 3 relates to the electrode delivery device according to Example 1, wherein the paddle has a length that is shorter than a length of the sleeve lumen such that a combination of the paddle and the irrigation/suction sleeve is relatively flexible.

Example 4 relates to the electrode delivery device according to Example 1, wherein the irrigation/suction sleeve is flexible.

Example 5 relates to the electrode delivery device according to Example 1, wherein a longitudinal axis of the paddle is disposed at an angle ranging from about 90 degrees to about 180 degrees in relation to a longitudinal axis of the proximal elongate shaft.

Example 6 relates to the electrode delivery device according to Example 5, wherein the longitudinal axis of the paddle is disposed at an angle of about 90 degrees in relation to the longitudinal axis of the proximal elongate shaft.

Example 7 relates to the electrode delivery device according to Example 5, wherein the longitudinal axis of the paddle is disposed at an angle of about 120 degrees in relation to the longitudinal axis of the proximal elongate shaft.

Example 8 relates to the electrode delivery device according to Example 5, wherein the longitudinal axis of the paddle is disposed at an angle of about 180 degrees in relation to the longitudinal axis of the proximal elongate shaft.

In Example 9, a fan-like cortical electrode device comprises at least two electrode segments, wherein each of the at least two electrode segments comprises a thin film pad, a plurality of electrode contacts disposed on the thin film pad, and a proximal connector attached to a proximal end of the thin film pad. Further, the at least two electrode segments are nestable in deployment such that the thin film pad of each of the at least two electrodes segments is disposed adjacent to each other and the proximal connector of each of the at least two electrode segments is disposed in a stacked configuration such that the proximal connector of each of the at least two electrode segments can be disposed through a single opening in a skull of the patient.

Example 10 relates to the fan-like cortical electrode device according to Example 9, wherein the thin film pad comprises a substantially triangular or pie slice shape.

Example 11 relates to the fan-like cortical electrode device according to Example 9, wherein each of the at least two electrode segments are nestable in deployment such that the at least two electrode segments form a portion of a circle in which the plurality of electrode contacts are optimally disposed across a surface of a brain of the patient.

Example 12 relates to the fan-like cortical electrode device according to Example 11, wherein each of the at least two electrode segments are nestable in deployment such that the at least two electrode segments form at least a half circle.

Example 13 relates to the fan-like cortical electrode device according to Example 11, wherein each of the at least two electrode segments are nestable in deployment such that the at least two electrode segments form a full circle.

Example 14 relates to the fan-like cortical electrode device according to Example 9, wherein the thin film pad comprises a first thin film layer and a second thin film layer, wherein the plurality of electrode contacts are disposed between the first and second thin film layers.

Example 15 relates to the fan-like cortical electrode device according to Example 9, wherein the thin film pad comprises rounded corners.

Example 16 relates to the fan-like cortical electrode device according to Example 9, wherein the thin film pad comprises at least one suture opening defined therein.

In Example 17, a method of implanting an intracranial electrode device comprises forming a hole in a skull of a patient, positioning a cortical electrode device on a delivery device, inserting the cortical electrode device through the hole with the delivery device to a target intracranial position, positioning the cortical electrode device at the target intracranial position via the delivery device, and removing the delivery device. The delivery device comprises a proximal elongate shaft and a paddle coupled to a distal end of the proximal shaft, the paddle comprising a paddle lumen defined within the paddle, and a plurality of holes defined in the paddle. The delivery device further comprises an irrigation/suction sleeve disposable over the paddle, the irrigation/ suction sleeve comprising a sleeve lumen defined within the sleeve and a plurality of holes defined in the sleeve.

Example 18 relates to the method according to Example 17, wherein the positioning the cortical electrode device on the delivery device comprises positioning the cortical electrode device on the paddle.

Example 19 relates to the method according to Example 17, further comprising applying a vacuum through the plurality of holes defined in the sleeve during the inserting the cortical electrode device to help retain the cortical electrode device on the paddle.

Example 20 relates to the method according to Example 17, further comprising delivery fluid through the plurality of holes defined in the sleeve prior to or during the removing the delivery device to help separate the paddle and the cortical electrode device.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIG. 12A is a view of a segment of the electrode as it would appear after being deployed.

FIG. 12B is a view of a segment of the electrode as it would appear after being deployed.

FIG. 12C is a view of a segment of the electrode as it would appear after being deployed.

FIG. 12D is a view of a segment of the electrode as it would appear after being deployed.

FIG. 12E is a view of a segment of the electrode as it would appear after being deployed.

DETAILED DESCRIPTION

The various embodiments disclosed or contemplated herein relate to improved systems, devices, and methods, and various components thereof, for recording neurological signals in the human body. More specifically, the implementations relate to various cortical electrode systems and devices for monitoring, stimulating, and/or ablating brain tissue, and various components of such systems and devices. Further, certain embodiments relate specifically to a cortical electrode system having a delivery device and a cortical electrode device. In certain exemplary implementations, the various systems and devices incorporate ultra-thin dielectric materials with conductive materials placed thereon, thereby resulting in multiple conductors in high density on the devices, which improves the resolution of signal gathering per channel.

Figure 1A:
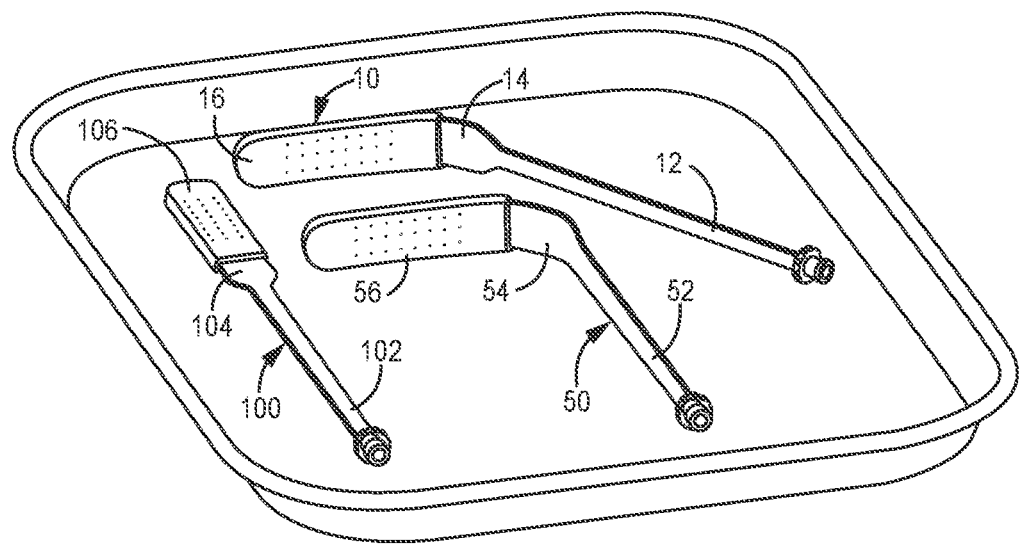
FIG. 1A is a view of three embodiments of the delivery device.
Figure 1B:
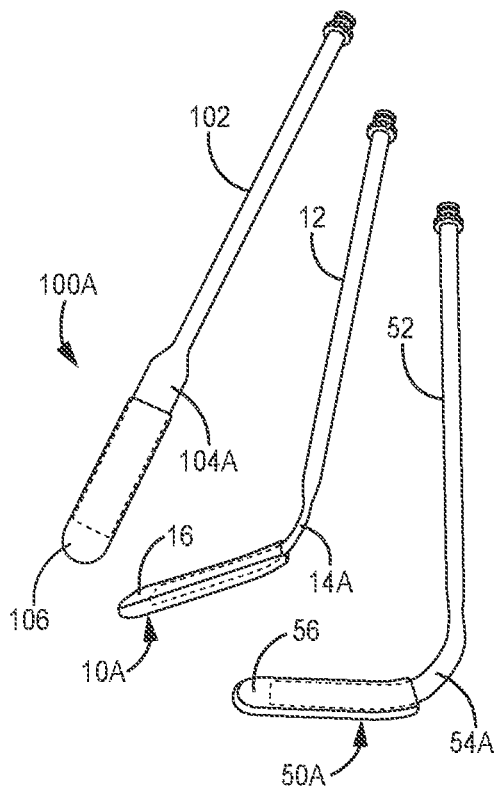
FIG. 1B is a view of three embodiments of the delivery device in the rigid form.
Figure 1C:
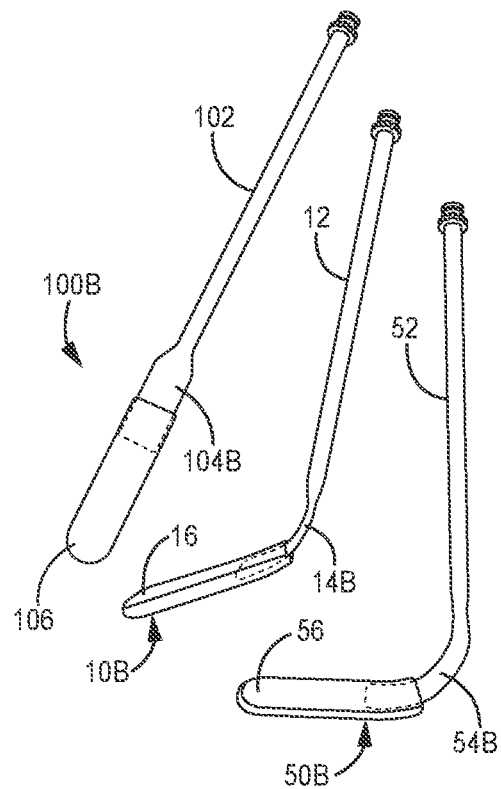
FIG. 1O is a view of three embodiments of the delivery device in the flexible form.

FIG. 1A-1C depict three different versions of a delivery device, including a 120-degree curved delivery device 10, a 90-degree curved delivery device 50, and a flat delivery device 100. FIG. 1A is a general depiction of the 120-degree curved delivery device 10, the 90-degree curved delivery device 50, and the flat delivery device 100. FIG. 1B depicts a rigid version of each the 120-degree curved delivery device 10A, 90-degree curved delivery device 50A, and flat delivery device 100A, each of which will be discussed in further detail below. In contrast, FIG. 10 depicts a flexible version of each the 120-degree curved delivery device 10B, 90-degree curved delivery device 50B, and flat delivery device 100B, all of which will also be discussed below. While only three embodiments are discussed herein, the delivery device can have any angular disposition between the flat embodiment (180 degrees) and the 90-degree curved embodiment). Therefore, it is understood that the delivery device is not limited to the three specific angular embodiments described in detail herein.

Figure 2A:
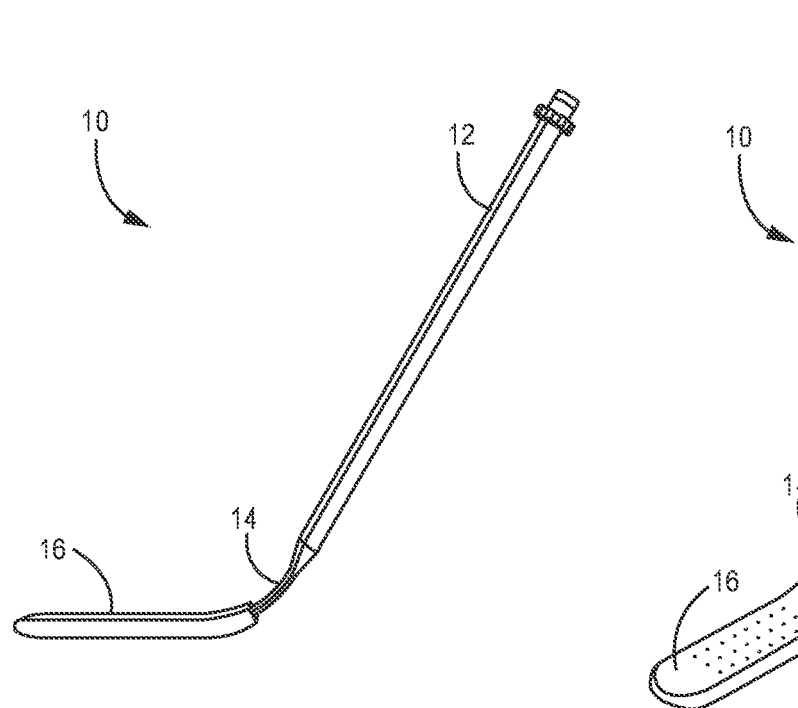
FIG. 2A is a side view of the 120-degree curved embodiment of the delivery device.
Figure 2B:
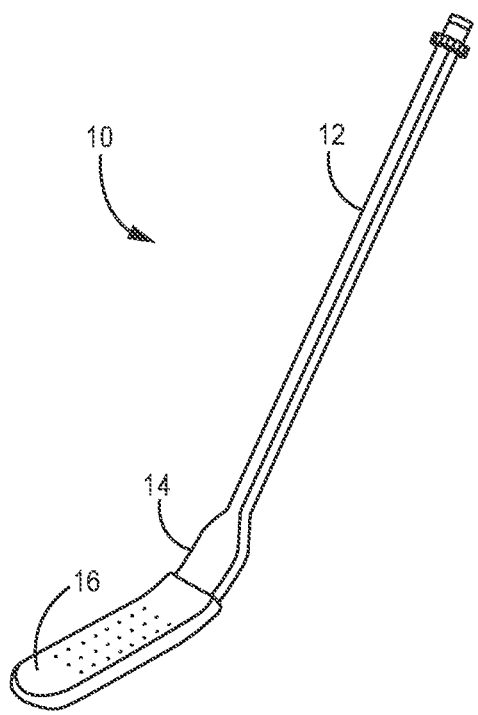
FIG. 2B is an angled view of the 120-degree curved embodiment of the delivery device.
Figure 2C:
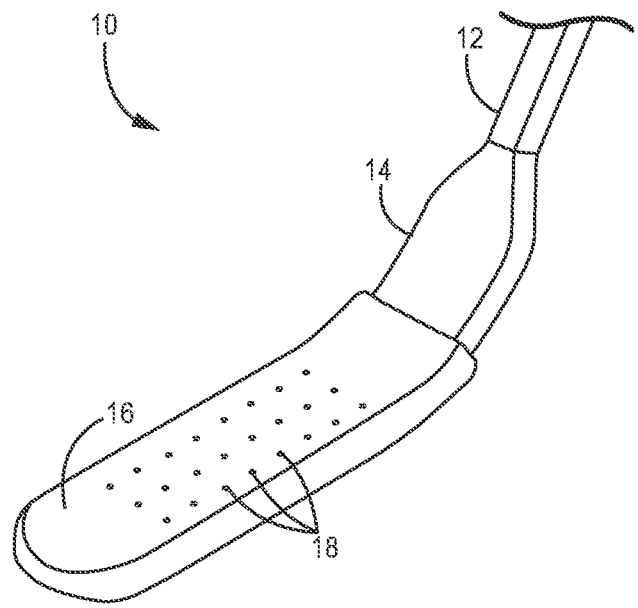
FIG. 2C is an enlarged view of the distal paddle for the 120-degree curved embodiment.
Figure 3A:
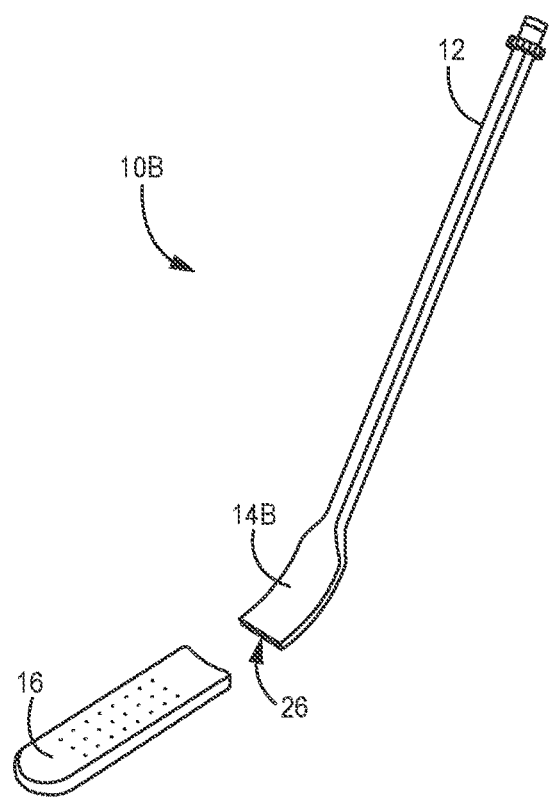
FIG. 3A is a view of the flexible form of the 120-degree curved embodiment with the irrigation/suction sleeve removed from the distal paddle.
Figure 3B:
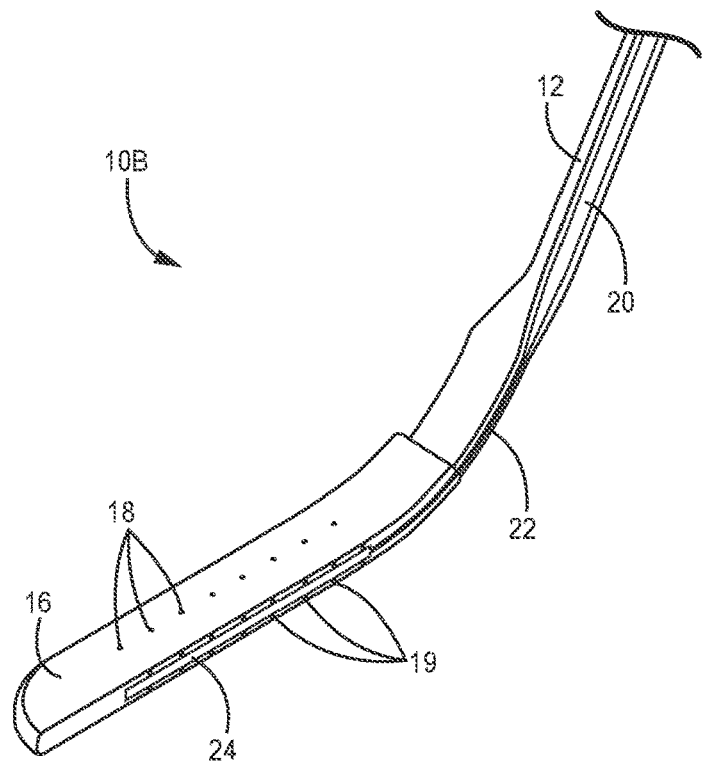
FIG. 3B is a cross-section of the flexible form of the 120-degree curved embodiment with the irrigation/suction sleeve positioned on the distal paddle.
Figure 4A:
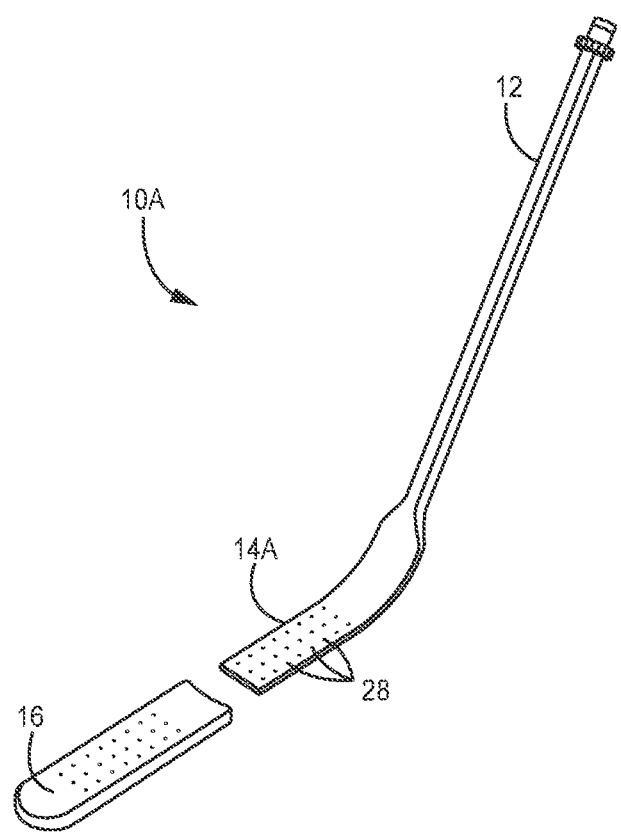
FIG. 4A is a view of the rigid form of the 120-degree curved embodiment with the irrigation/suction sleeve removed from the distal paddle.
Figure 4B:
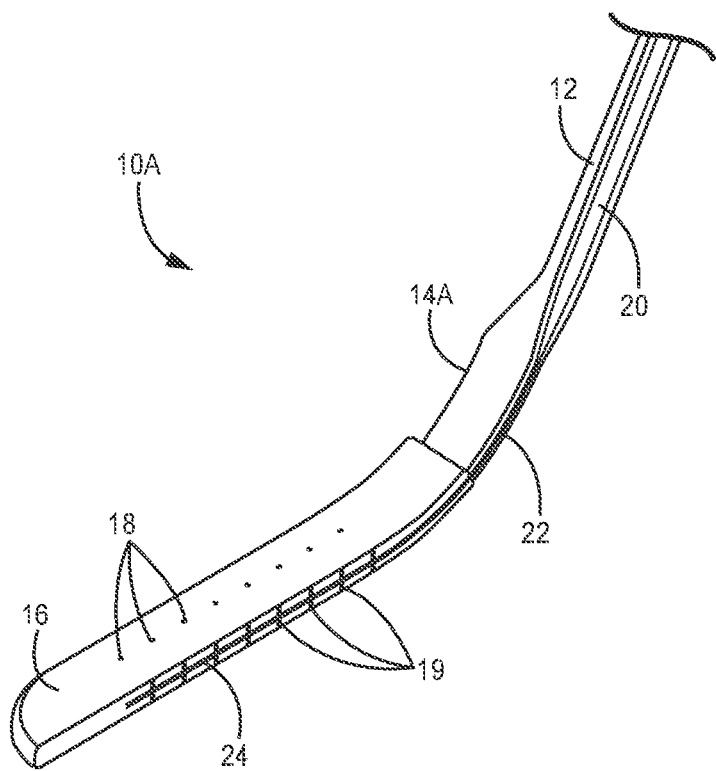
FIG. 4B is a cross-section of the rigid form of the 120-degree curved embodiment with the irrigation/suction sleeve positioned on the distal paddle.

FIGS. 2A-4B depict the 120-degree curved delivery device 10 in further detail, with FIGS. 2A-2C depicting a generic version of the device 10 that could be either rigid or flexible, FIGS. 3A and 3B depicting the flexible version of the device 10B and FIGS. 4A and 4B depicting the rigid version of the device 10A, As depicted in FIGS. 2A and 2B, both the rigid embodiment and the flexible embodiment have many of the same components. That is, the device 10 has a proximal elongate shaft (also referred to herein as a "tube") 12 and distal paddle 14 attached to or extending from the distal end of the shaft 12 such that the longitudinal axis of distal paddle 14 is disposed at about a 120-degree angle in relation to the longitudinal axis of the proximal tube 12. The elongate shaft 12 in this embodiment and any other delivery device embodiment disclosed or contemplated herein can be a tube, a rod, or any other elongate structure that can be attached to or integral with the paddle 14. The paddle 14 in this embodiment and any other delivery device embodiment disclosed or contemplated herein is any structure having substantially flat upper and lower surfaces that are both wider and longer than the height of the structure such that the paddle 14 has a blade-like structure.

FIGS. 2A and 2B also depict an irrigation/suction sleeve 16, which is slidably positionable on the distal paddle 14. The sleeve 16 is any flexible structure having an opening and an interior such that the paddle 14 can be positioned through the opening and into the interior thereof, whereby the sleeve 16 encompasses and/or covers at least a portion of the paddle 14 as shown. FIG. 2C further depicts an irrigation/suction sleeve 16 where the top of the irrigation/suction sleeve 16 has a plurality of holes 18 defined therein, the bottom of the irrigation/suction sleeve 16 has a plurality of holes 19 defined therein, and the sleeve 16 further has a lumen 24 (best shown in FIG. 3B), which is defined within and along the length of irrigation/suction sleeve 16 and is in fluidic communication with the top holes 18 and the bottom holes 19. Alternatively, the sleeve 16 can have only top holes 18 or only bottom holes 19.

Further, as best shown in FIGS. 3B and 4B, proximal tube 12 has a lumen 20 defined therethrough and distal paddle 14 has a lumen 22 defined therethrough as well, such that lumen 20 and lumen 22 are in fluidic communication and such that when irrigation/suction sleeve 16 is disposed over distal paddle 14, the irrigation/suction sleeve lumen 24 is in fluidic communication with proximal tube lumen 20 and distal paddle lumen 22. During use, either fluid can be delivered and/or a vacuum can be applied via the device 10. More specifically, fluid can be delivered through the proximal tube lumen 20, and through distal paddle lumen 22 and irrigation/suction sleeve lumen 24, then out through top holes 18 and bottom holes 19. Similarly, a vacuum can be applied via the proximal tube lumen 20 such that the vacuum is applied through the distal paddle lumen 22 and the sleeve lumen 24, and thus via the top and bottom holes 18, 19, thereby resulting in suction at the holes 18, 19.

FIGS. 3A and 3B depict the flexible tip 120-degree curved delivery device 10B, such that the flexibility of the flexible tip results from the short distal paddle 14B. When irrigation/suction sleeve 16 is placed over the short distal paddle 14B, the short distal paddle 14B does not span the entire length of irrigation/suction sleeve 16. Instead, only a proximal length of irrigation/suction sleeve 16 is disposed over paddle 14B, resulting in flexibility the portion of the irrigation/suction sleeve 16 that extends distally beyond the short distal paddle 14B. Additionally, FIG. 3A shows short distal paddle 14 with a distal opening 26 providing fluidic access to the distal paddle lumen 22.

FIGS. 4A and 4B depict the rigid tip 120-degree curved delivery device 10A, such that the rigid tip results from a long distal paddle 14A. When irrigation/suction sleeve 16 is placed over the long distal paddle 14A, the long distal paddle 14A spans almost the entire length of irrigation/suction sleeve 16. Because the long distal paddle 14A extends almost the entire length of irrigation/suction sleeve 16, and because the paddle 14A is more rigid than the sleeve 16, the result is that the combination of the long distal paddle 14A and the irrigation/suction sleeve 16 is significantly more rigid in comparison to the flexible tip device 10B. Additionally, FIG. 4A shows long distal paddle 14A further comprised of top holes 28 that are in fluidic communication with the irrigation/suction sleeve lumen 24 and the irrigation/suction sleeve top holes 18. It is understood that the paddle 14A also has bottom holes (not shown) that are in fluidic communication with the bottom holes 19 of the sleeve 16.

It is understood that any of the paddle embodiments disclosed or contemplated herein (including, for example, the paddles 14A, 14B or any other paddle embodiment discussed below) can be made of various metals or polymers. For example, the paddles can be made of at least one metal such as stainless steel, various other metals, and/or any combination thereof. Similarly, the paddles can be made of at least one polymer such as, for example, polycarbonate, Ultem, acrylonitrile butadiene styrene (ABS), polypropylene, and/or polyethylene, or any combination thereof. It is further understood that any of the proximal tube embodiments disclosed or contemplated herein (including, for example, the tube 12 or any other tube embodiment discussed below) can be made of at least one polymer such as, for example, polycarbonate, Ultem, acrylonitrile butadiene styrene (ABS), polypropylene, and/or polyethylene, or any combination thereof. Further, any of the irrigation/suction sleeve embodiments disclosed or contemplated herein (including, for example, the sleeve 16 or any other sleeve embodiment discussed below) can be made of at least one polymer such as, for example, silicone, urethane, nylon, polypropylene, and/or polyethylene, or any combination thereof. In a further alternative embodiment, any of the sleeve embodiments disclosed or contemplated herein can also have a coating disposed thereon, such as, for example, a hydrophobic coating made of silicone or any similar polymer. Alternatively, the coating can be, for example, a hydrophilic coating made of a modified polyester or polyurethane or any similar polymer. Such coatings can aid in the tackiness or lubricity of the sleeve.

Figure 5A:
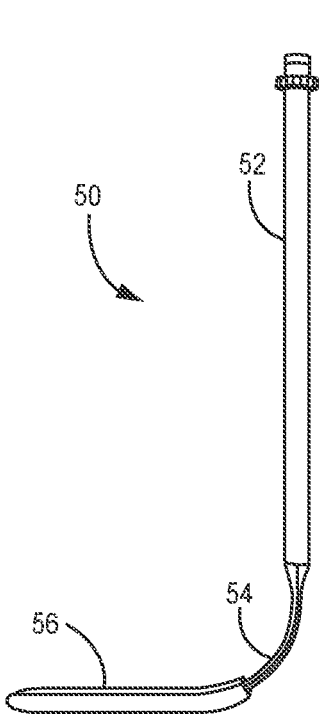
FIG. 5A is a side view of the 90-degree curved embodiment of the delivery device.
Figure 5B:
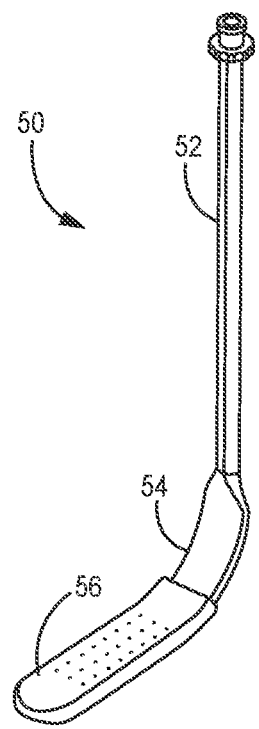
FIG. 5B is an angled view of the 90-degree curved embodiment of the delivery device.
Figure 5C:
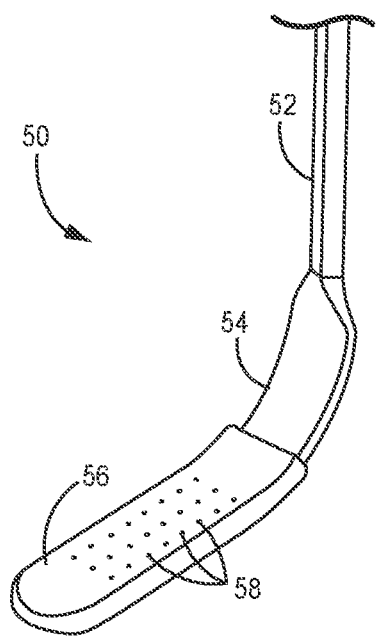
FIG. 5C is an enlarged view of the distal paddle for the 90-degree curved embodiment.
Figure 6A:
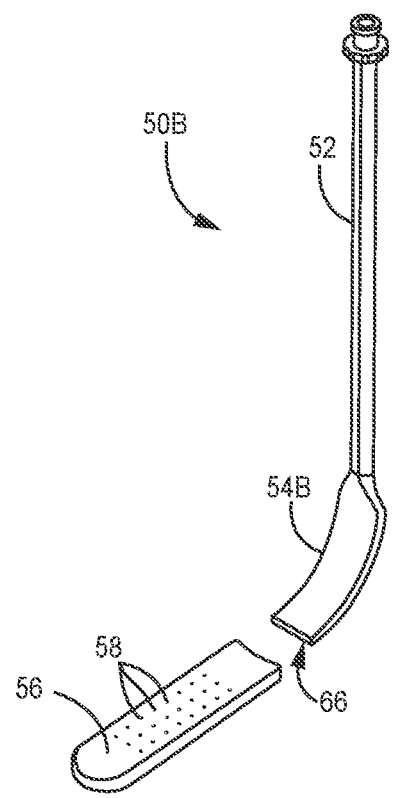
FIG. 6A is a view of the flexible form of the 90-degree curved embodiment with the irrigation/suction sleeve removed from the distal paddle.
Figure 6B:
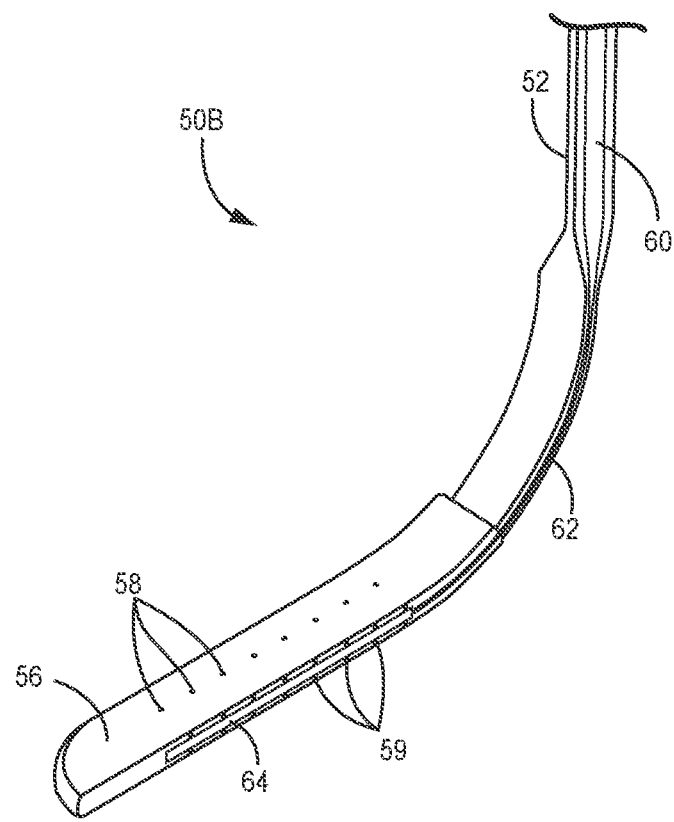
FIG. 6B is a cross-section of the flexible form of the 90-degree curved embodiment with the irrigation/suction sleeve positioned on the distal paddle.
Figure 7A:
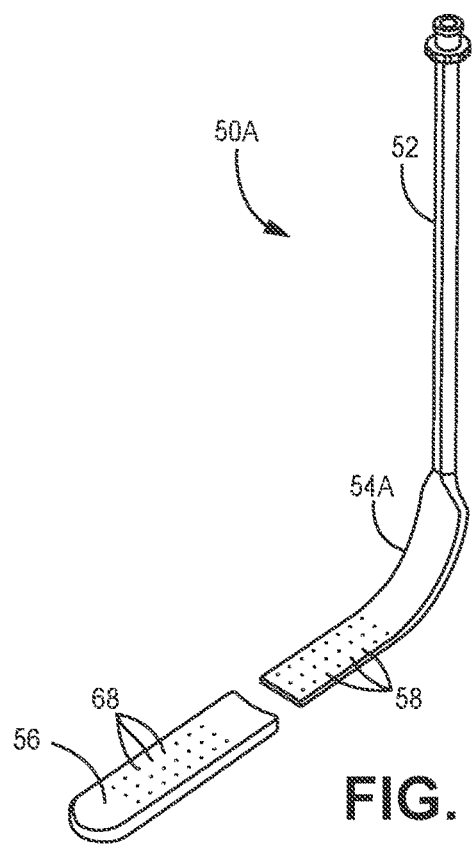
FIG. 7A is a view of the rigid form of the 90-degree curved embodiment with the irrigation/suction sleeve removed from the distal paddle.
Figure 7B:
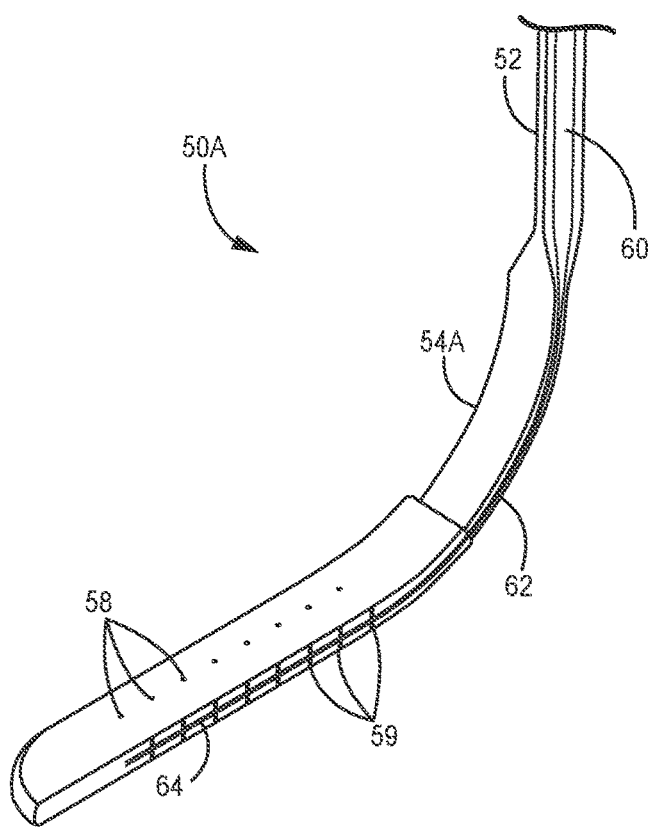
FIG. 7B is a cross-section of the rigid form of the 90-degree curved embodiment with the irrigation/suction sleeve positioned on the distal paddle.

FIGS. 5A-7B depict the 90-degree curved delivery device 50 in further detail, with FIGS. 5A-5C depicting a generic version of the device 50 that could be either rigid or flexible, FIGS. 6A and 6B depicting the flexible version of the device 50B and FIGS. 7A and 7B depicting the rigid version of the device 50A. FIGS. 5A and 5B show the 90-degree curved delivery device 50 (which could be the flexible or rigid version) having a proximal tube 52 and distal paddle 54 in which the longitudinal axis of distal paddle 54 is disposed at about a 90-degree angle in relation to the longitudinal axis of the proximal tube 52. The device 50 also has an irrigation/suction sleeve 56 which is slidably positionable on the distal paddle 54. FIG. 5C further depicts irrigation/suction sleeve 56 where the top of the irrigation/suction sleeve 56 has a plurality of holes 58 defined therein, the bottom of the irrigation/suction sleeve 56 has a plurality of holes 59 defined therein, and further has a lumen 64 (best shown in FIG. 6B) defined along the length of irrigation/suction sleeve 56 and in fluidic communication with the top holes 58 and the bottom holes 59. Alternatively, the sleeve 56 can have only top holes 58 or only bottom holes 59.

Further, as best shown in FIGS. 6B and 7B, proximal tube 52 has a lumen 60 defined therethrough and the distal paddle 54 has a lumen 62 defined therethrough as well, such that lumen 60 and lumen 62 are in fluidic communication and such that when irrigation/suction sleeve 56 is disposed over distal paddle 54, the irrigation/suction sleeve lumen 64 is in fluidic communication with proximal tube lumen 60 and distal paddle lumen 62. During use, either fluid can be delivered and/or a vacuum can be applied via the device 50. More specifically, fluid can be delivered through the proximal tube lumen 60, through distal paddle lumen 62 and irrigation/suction sleeve lumen 64, and then out through top holes 58 and bottom holes 59. Similarly, a vacuum can be applied via the proximal tube lumen 60 such that the vacuum is applied through the distal paddle lumen 62 and the sleeve lumen 64, and thus via the top and bottom holes 58, 59, thereby resulting in suction at the holes 58, 59.

FIGS. 6A and 6B depict the flexible tip 90-degree curved delivery device 50B, such that the flexibility of the flexible tip results from the short distal paddle 54B. When irrigation/suction sleeve 56 is placed over the short distal paddle 54B, the short distal paddle 54B does not span the entire length of irrigation/suction sleeve 56. Instead, only a proximal length of irrigation/suction sleeve 56 is disposed over paddle 54B, resulting in flexibility of the portion of the irrigation/suction sleeve 56 that extends distally beyond the short distal paddle 54B. Additionally, FIG. 6A shows short distal paddle 54 with a distal opening 66 providing fluidic access to the distal paddle lumen 62.

FIGS. 7A and 7B depict the rigid tip 90-degree curved delivery device 50A, such that the rigid tip results from a long distal paddle 54A. When irrigation/suction sleeve 56 is placed over the long distal paddle 54A, the long distal paddle 54A spans almost the entire length of irrigation/suction sleeve 56. Because the long distal paddle 54A extends almost the entire length of irrigation/suction sleeve 56, and because the paddle 54A is more rigid than the sleeve 56, the result is that the combination of the long distal paddle 54A and the irrigation/suction sleeve 56 is significantly more rigid in comparison to the flexible tip device 50B. Additionally, FIG. 7A shows long distal paddle 54A further comprised of holes 68 that are in fluidic communication with the irrigation/suction sleeve lumen 64 and the irrigation/suction sleeve top holes 58. It is understood that the paddle 54A also has bottom holes (not shown) that are in fluidic communication with the bottom holes 59 of the sleeve 56.

Figure 8A:
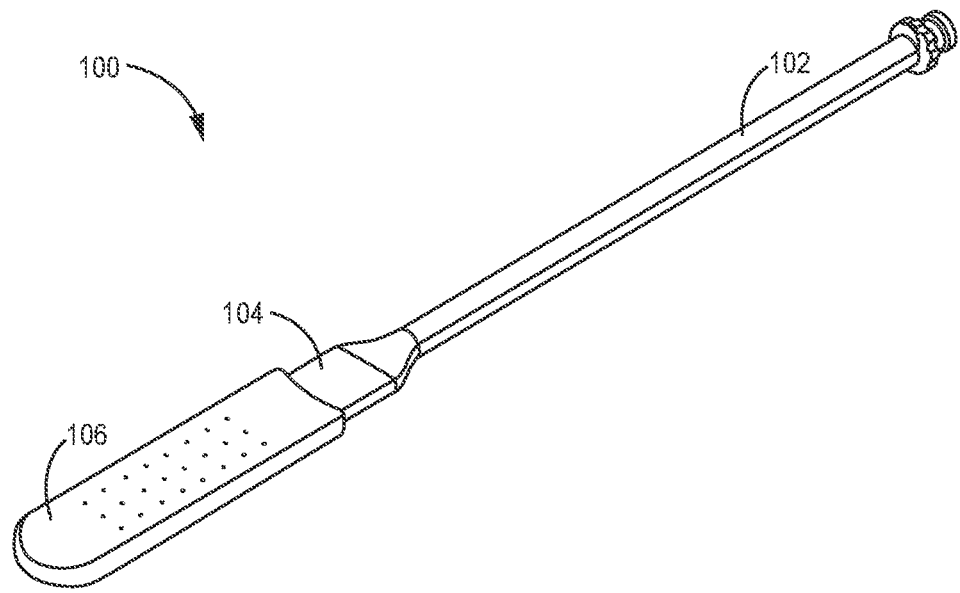
FIG. 8A is a view of the flat embodiment of the delivery device.
Figure 8B:
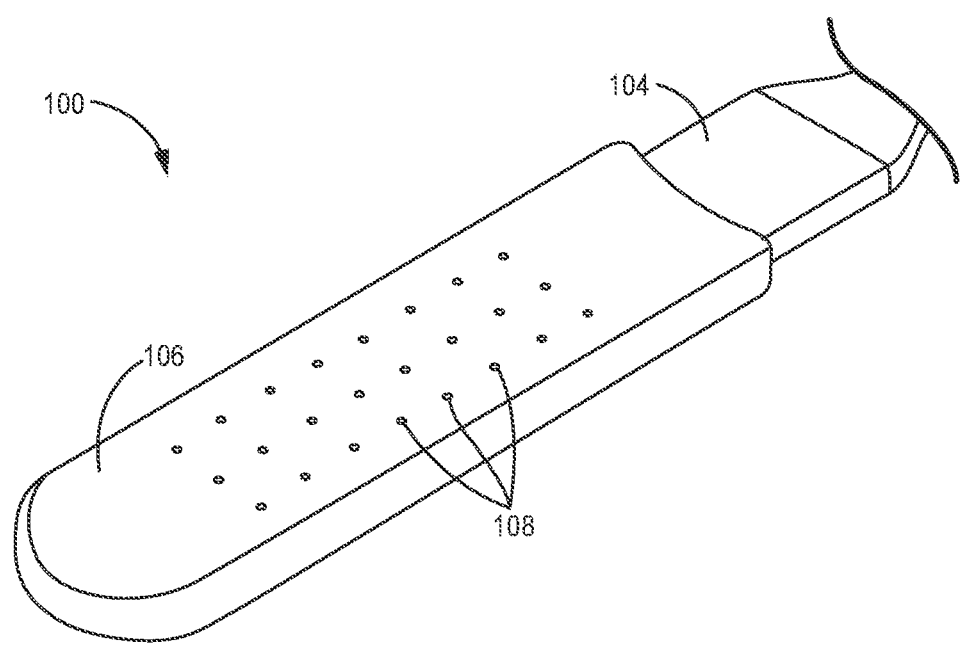
FIG. 8B is an enlarged view of the distal paddle for the flat embodiment.
Figure 9A:
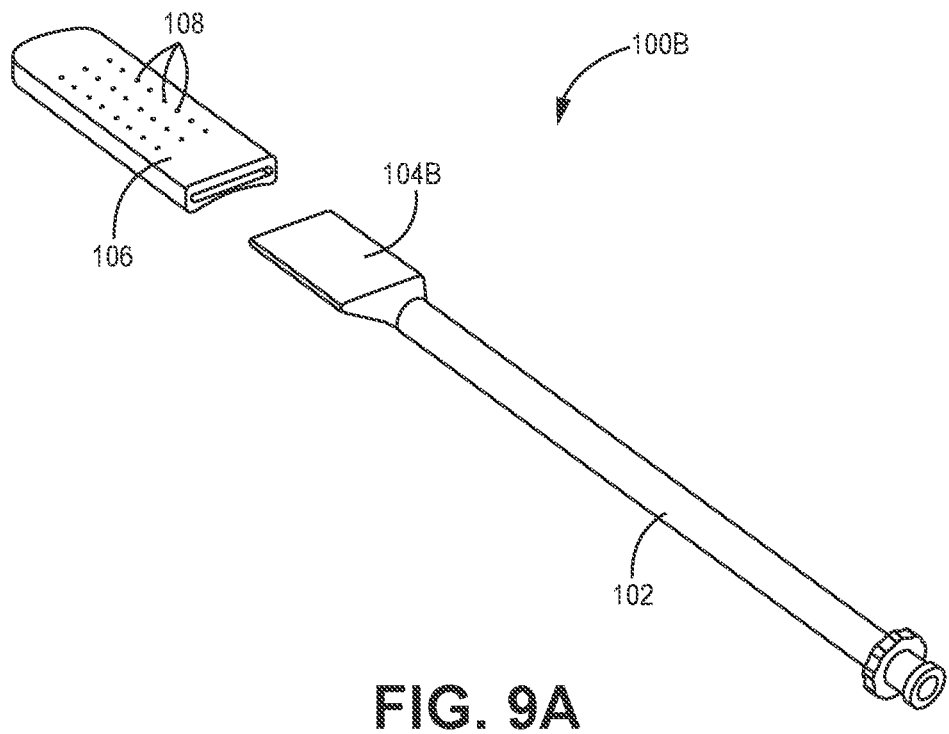
FIG. 9A is a view of the flexible form of the flat embodiment with the irrigation/suction sleeve removed from the distal paddle.
Figure 9B:
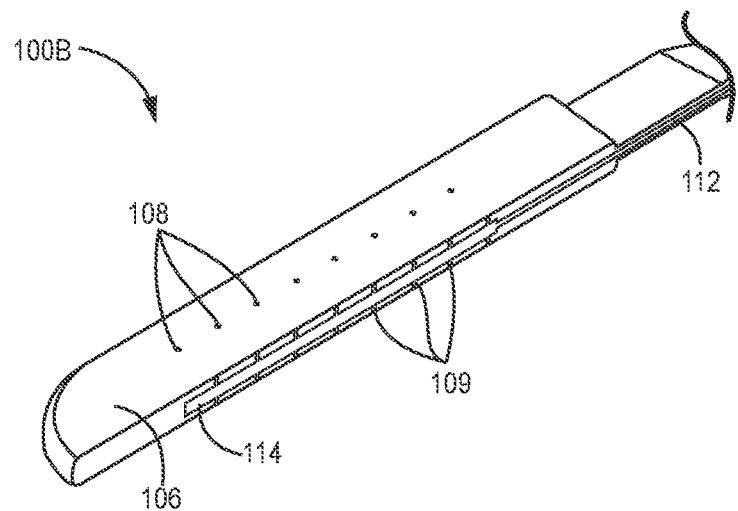
FIG. 9B is a cross-section of the flexible form of the flat embodiment with the irrigation/suction sleeve positioned on the distal paddle.
Figure 10A:
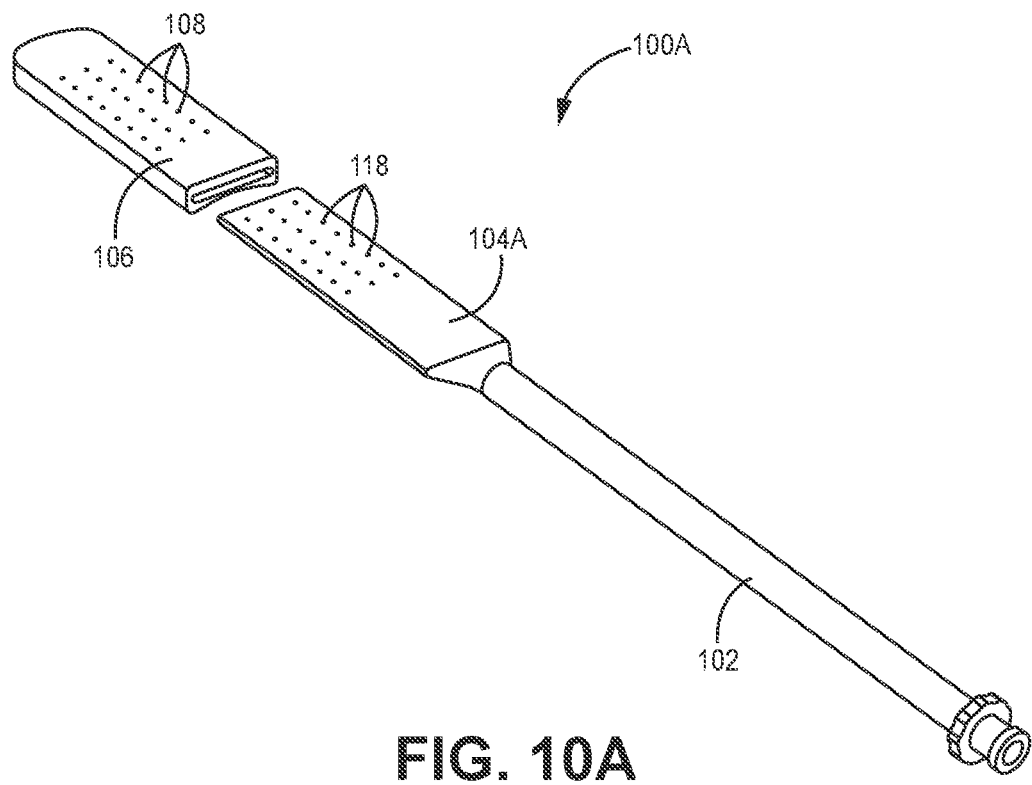
FIG. 10A is a view of the rigid form of the flat embodiment with the irrigation/suction sleeve removed from the distal paddle.
Figure 10B:
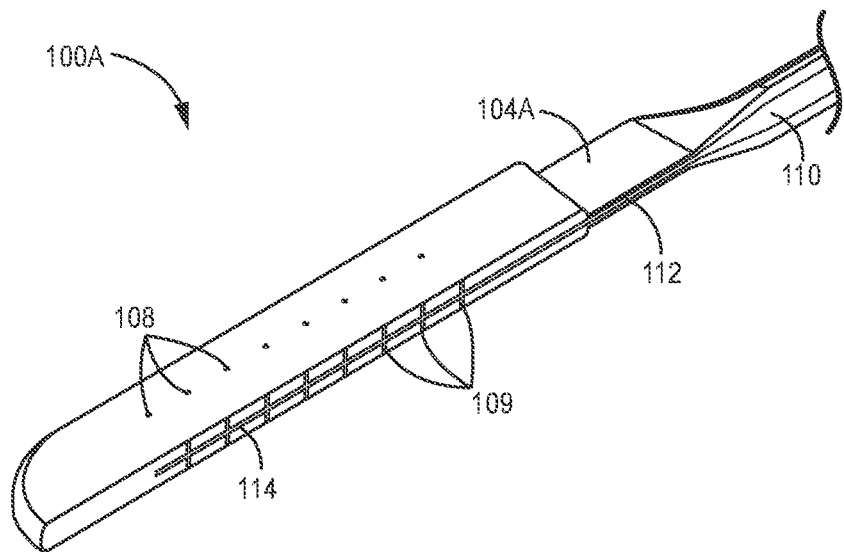
FIG. 10B is a cross-section of the rigid form of the flat embodiment with the irrigation/suction sleeve positioned on the distal paddle.

FIGS. 8A-10B depict the flat delivery device 100 in further detail, with FIGS. 8A and 8B depicting a generic version of the device 100 that could be either rigid or flexible, FIGS. 9A and 9B depicting the flexible version of the device 100B and FIGS. 10A and 10B depicting the rigid version of the device 100A. FIGS. 2A and 2B show the flat delivery device 100, which has a proximal tube 102 and a distal paddle 104 in which the longitudinal axis of distal paddle 104 is in line with the longitudinal axis of the proximal tube 102. Further, the device 100 has an irrigation/suction sleeve 106 which is slidably positionable on the distal paddle 104. FIG. 8B depicts irrigation/suction sleeve 106 in greater detail, where the top of the irrigation/suction sleeve 106 has a plurality of holes 108 defined therein and the bottom of irrigation/suction sleeve 106 has a plurality of holes 109 defined therein. Irrigation/suction sleeve 106 also comprises a lumen 114 (best shown in FIG. 9B) defined along the length of irrigation/suction sleeve 106 and in fluidic communication with top holes 108 and bottom holes 109. Alternatively, the sleeve 106 can have only top holes 108 or only bottom holes 109.

Further, as best shown in FIGS. 9B and 10B, the proximal tube 102 has a lumen 110 defined therethrough, and the distal paddle 104 has a lumen 112 defined therethrough as well, such that lumen 110 and lumen 112 are in fluidic communication and such that when irrigation/suction sleeve 106 is disposed over distal paddle 104, the irrigation/suction sleeve lumen 114 is in fluidic communication with proximal tube lumen 110 and distal paddle lumen 112. During use, either fluid can be delivered and/or a vacuum can be applied via the device 100. More specifically, fluid can be delivered through the proximal tube lumen 110, and through distal paddle lumen 112 and irrigation/suction sleeve lumen 114, then out through top holes 108 and bottom holes 109. Similarly, a vacuum can be applied via the proximal tube lumen 110 such that the vacuum is applied through the distal paddle lumen 112 and the sleeve lumen 114, and thus via the top and bottom holes 108, 109, thereby resulting in suction at the holes 108, 109.

FIGS. 9A and 9B depict the flexible tip flat delivery device 100B, such that the flexibility of flexible tip results from the short distal paddle 104B. When irrigation/suction sleeve 106 is placed over the short distal paddle 104B, the short distal paddle 104B does not span the entire length of irrigation/suction sleeve 106. Instead, only a proximal length of irrigation/suction sleeve 106 is disposed over paddle 104B, resulting in flexibility of the portion of the irrigation/suction sleeve 106 that extends distally beyond the short distal paddle 104B. The short distal paddle 104 is also further comprised of a distal opening 116 providing fluidic access to the distal paddle lumen 112.

FIGS. 10A and 10B depict the rigid tip flat delivery device 100A, such that the rigid tip results from a long distal paddle 104A. When irrigation/suction sleeve 106 is placed over the long distal paddle 104A, the long distal paddle 104A spans almost the entire length of irrigation/suction sleeve 106. Because the long distal paddle 104A extends almost the entire length of irrigation/suction sleeve 106, and because the paddle 104A is more rigid than the sleeve 106, the result is that the combination of the long distal paddle 104A and the irrigation/suction sleeve 106 is significantly more rigid in comparison to the flexible tip device 100B. Additionally, FIG. 10A shows long distal paddle 104A further comprised of holes 118 that are in fluidic communication with the irrigation/suction sleeve lumen 114 and the irrigation/suction sleeve top holes 108. It is understood that the paddle 104A also has bottom holes (not shown) that are in fluidic communication with the bottom holes 109 of the sleeve 106. Alternatively, the paddle 104A can have only top holes 118 or only bottom holes 109. It is further understood that any of the paddle embodiments disclosed or contemplated herein in any of the various device embodiments disclosed or contemplated herein can have top and bottom holes, only top holes, or only bottom holes in a similar fashion to the sleeve disposed onto the paddle.

Figure 11:
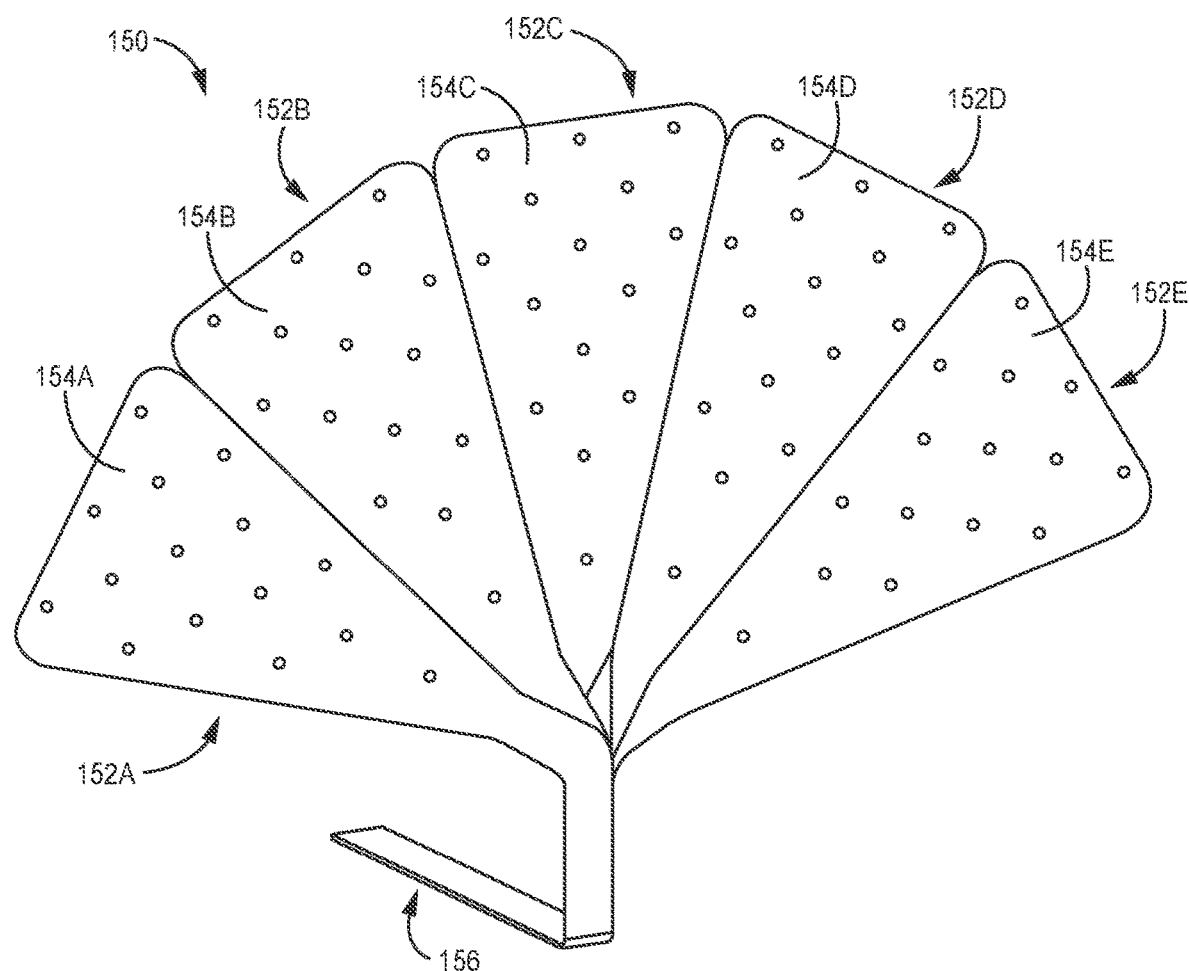
FIG. 11 is a view of the electrode in its deployed configuration, according to one embodiment.

Various embodiments of the system as contemplated herein also relate to cortical electrodes that can be delivered by the various delivery devices disclosed or contemplated herein. For example, FIGS. 11-12E depict one embodiment of a cortical electrode 150 having five separate electrode segments 152A, 152B, 152C, 152D, 152E that can be deployed together in a nested fashion as described in further detail below. The fan-like configuration, according to one embodiment, is depicted in FIG. 11, in which the five separate electrode segments 152A-152E are deployed at a desired location in the subdural space of a patient in a nested fashion (with each of the segments 152A-152E disposed through the same opening in the patient's skull). The nested positioning of the segments 152A-152E form the fan-like configuration as shown, with the leads 156 stacked together such that all of the leads 156 can be positioned through the single opening in the patient's skull.

As best shown in FIGS. 12A-12E, each electrode segment 152A-152E has a pad 154A-154E and a lead 156A-156E. As with known cortical electrodes, the pad 154A-E is the component that contains the array of contacts and is typically disposed in contact with the brain during use. Further, the lead 156A-E is an elongate connection component (also referred to herein as a "connector" or "elongate connector") 156A-E that extends from the pad 154A-E as shown such that it may be connected to an external monitoring mechanism in a fashion similar to other cortical electrodes. As such, each segment 152A-E is a separate, fully-functioning electrode that can function as an electrode separate and apart from each of the other segments 152A-E. In use, as described in detail below, the electrode 150 is, in certain embodiments, deployed in the fan-like configuration made up of a combination of all five segments 152A-E as best shown in FIG. 11.

The fan-like configuration of FIG. 11 allows for the five electrodes to have maximal or optimal coverage of the patient's brain. More specifically, the five pads 154A-154E are positioned adjacent to each other to ensure the maximum amount of coverage of the brain surface by the contacts on the pads 154A-154E. In certain embodiments, the contacts on each of the pads 154A-154E are spaced thereon to ensure that the entire brain surface on which the fan-like configuration of electrode segments 152A-152E are disposed is uniformly covered by the contacts, thereby ensuring uniform sensing and/or stimulation across that area.

It is understood that, according to various alternatives, the fan-like electrode 150 can be any size. That is, the electrode 150 made up of two, three, four, six, or any number of segments. It is further understood that more than one fan-like electrode 150 can be positioned within the subdural space such that the two or more fan-like electrodes 150 can form a full circle. Alternatively, the number of segments and/or the number of electrodes 150 can be modified to cover as small an amount of the surface as that covered by two pads and as large an amount of the surface as a full circle.

It is further understood that regardless of the number of segments and/or the number of fan-like electrodes, all of the leads 156 can be stacked to be positioned through the same opening.

Figure 13A:
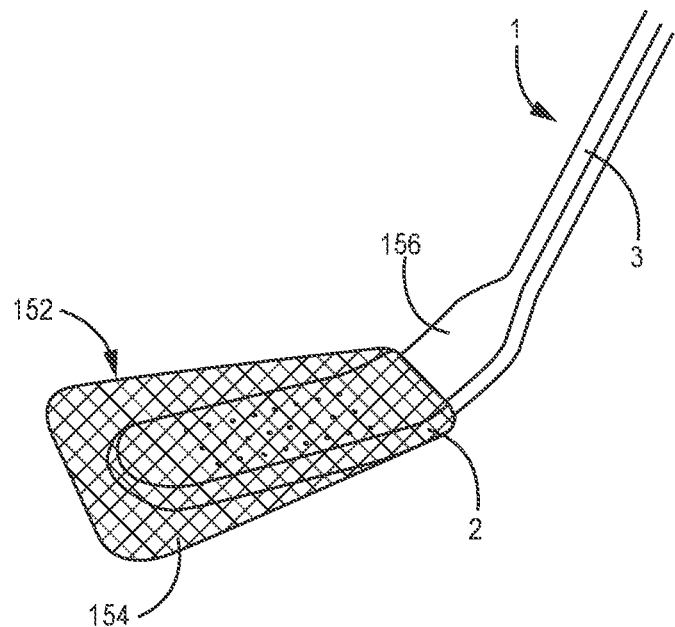
FIG. 13A depicts an electrode segment disposed on a delivery device, according to one embodiment.
Figure 13B:
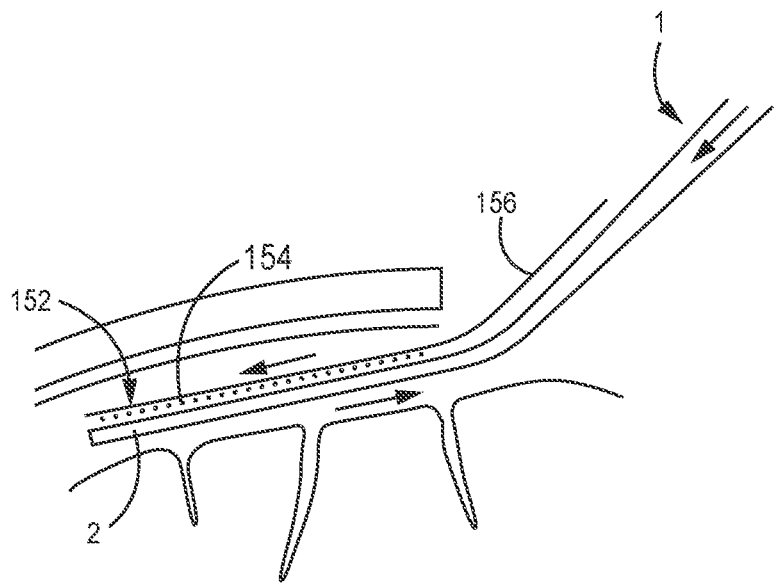
FIG. 13B depicts the electrode segment and delivery device of FIG. 13A being inserted through the skull and positioned on the brain of a patient, according to one embodiment.

FIGS. 13A-13B depict the use of the electrode delivery system, according to one embodiment. It is understood that any of the device embodiments disclosed or contemplated herein can be used to perform the forthcoming procedure. It is further understood that the delivery devices and the method as disclosed or contemplated herein can be used to deliver other cortical electrode devices.

In certain implementations, an electrode delivery device 1 (which can be any of the delivery device embodiments disclosed or contemplated herein) is used to insert an electrode segment 152 (which can be any segment disclosed or contemplated herein, or any other known cortical electrode) into the desired location in contact with the brain of the patient. First, as best shown in FIG. 13A, the electrode segment 152 is positioned on the delivery device 1 prior to insertion into the patient. More specifically, the segment pad 154 is positioned on the irrigation/suction sleeve 2 as shown such that the lead (or "tail") 156 extends away from the pad 154 along and adjacent to the proximal tube 3 of the delivery device 1. In certain embodiments, the sleeve 2 is made of silicone or a material containing at least some silicone as discussed above, and the electrode pad 154 will at least partially adhere to the sleeve 2 as a result of the properties of the silicone. Alternatively or additionally, a vacuum can be applied through the device 1 as described above such that suction is applied to the pad 154 via the paddle and sleeve 2, thereby helping to adhere or otherwise retain the pad 154 on the sleeve 2. This at least partial adherence facilitates the delivery of the segment 152 to the desired location in contact with the patient's brain. It is understood that other known electrode devices can also be disposed on the delivery device 1 in a similar fashion and similarly adhere to the sleeve 2.

Once the segment 152 has been positioned on the delivery device 1, the device 1 and segment 152 can be inserted through an opening in the skull and into the desired location in the subdural space to be placed on the brain, as depicted in FIG. 13B. The user (such as a surgeon) can hold onto both the lead 156 and the proximal tube 3, thereby helping to retain the segment 152 on the device 1 (along with the adherence of the pad 154 to the sleeve 2 as described above via the properties of the sleeve 2 and/or the suction applied thereby).

To aid insertion into the subdural space, the delivery device 1 may be used to exert downward pressure on the brain such that the electrode 152 can be placed in the right location. More specifically, a user can apply a downward force (toward the brain) to the proximal tube 3, thereby causing the paddle and sleeve 2 to apply force to the surface of the brain, thereby creating space between the brain and the dura. Additionally, fluid may be injected through proximal tube lumen 4 and out of the paddle and sleeve 2 as described in further detail above, which can aid movement of the electrode 152 and irrigation/suction sleeve 16 within the subdural space by reducing friction.

When the electrode 152 is positioned in the desired location, the delivery device 1 is removed. According to certain implementations, the removal of the delivery device 1 can be facilitated by delivering fluid through the device 1. More specifically, fluid can be delivered through proximal tube lumen 20 and out of the paddle and sleeve 2, thereby reducing the adherence of the electrode 152 to the sleeve 2. After the fluid is injected, the delivery device 1 may be removed from the subdural space while the electrode segment 152 stays in place on the brain. This process can be repeated until the desired number of segments 152 have been placed. When multiple segments 152 are used, the electrode segments 152A, 152B, 152C, 152D, 152E are placed in the fanned arrangement 150, which is best shown in FIG. 11.

Figure 14:
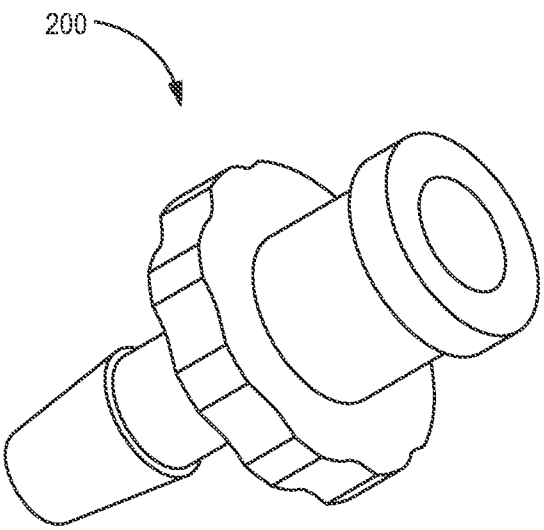
FIG. 14 depicts a proximal connector, according to one embodiment.

According to a further implementation as best shown in FIG. 14, any device embodiment disclosed or contemplated herein can have a proximal connector 200 coupled to the device. More specifically, the proximal connector 200 can be attached to a proximal end of the proximal tube of any device embodiment disclosed or contemplated herein. The connector 200, according to certain implementations, can be used to couple the device to an irrigation and/or suction/vacuum line. It is understood that any other known connector can be used as well.

Figure 15:
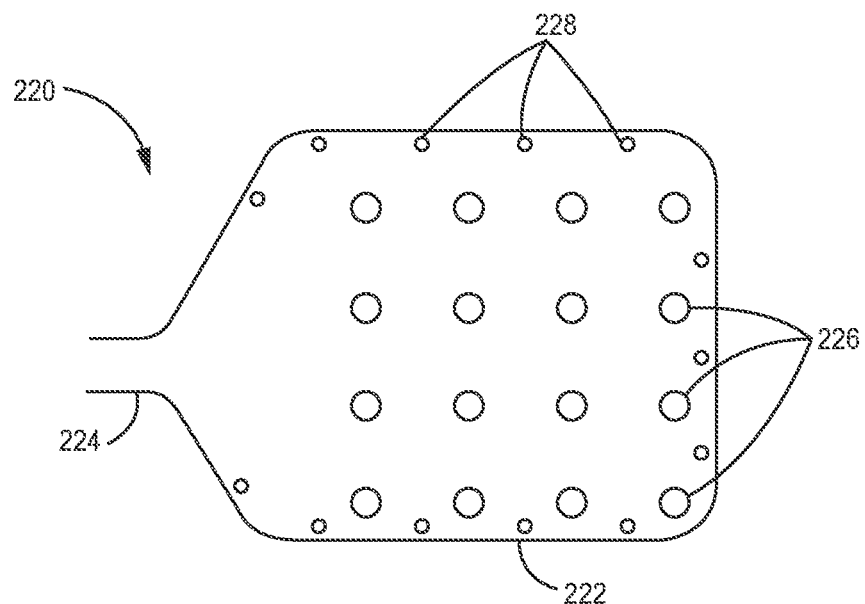
FIG. 15 depicts a cortical electrode, according to one embodiment.

Another electrode embodiment is depicted in FIG. 15, which illustrates a cortical electrode device 220 that can be used with any of the delivery device embodiments disclosed or contemplated herein. Further, it is understood that any of the features of this device 220 can be incorporated into any electrode device disclosed or contemplated herein. The neural probe device 220 as shown includes an electrode array (or "pad") 222 and a portion of an elongate connector (or "lead") 224. The pad 222 has a plurality of contacts 226 disposed on the pad 222. In addition, the pad 22 has a plurality of suture holes (or "openings") 228 formed in the pad 222 as shown. In one exemplary embodiment as shown, the holes 228 are formed adjacent to the sides or outer edges of the pad 222 in a spaced configuration. In use, the suture holes 228 allow for the threading of one or more sutures through the holes 228 such that the sutures can be used to attach the pad 222 to a target area of the brain surface. The holes 228 can be pre-formed holes 228 that are formed in the pad 222 via laser or any other known mechanism or procedure during the course of making or manufacturing the pad 222. As such, the electrode device 220 allows for use of the suture holes 228 by a surgeon without the need for the surgeon to form her own suture holes 228 during the course of the procedure.

In certain implementations, the contacts 226 can be dispersed across the pad 222 in a spaced configuration such that each of the contacts 226 is evenly spaced from the other contacts 226. Alternatively, the contacts 226 can be disposed on the pad 222 in any configuration. Further, it is understood that the pad 222 can be a thin-film pad 222. In one embodiment, the thin-film pad 222 is made of a polyimide material, such as Kapton® from DuPont®. Alternatively, the pad 222 can be made of any other known flexible material for use in intracranial electrode arrays. Further, it is understood that the pad 222 can be made according to a known process of laminating two layers of polyimide (or any other known material for this purpose) together with the electrode contacts (also referred to as "traces) therebetween and then using a laser to expose the contacts. Alternatively, the pad 222 can be made according to any known process. In accordance with one implementation, the openings 228 are formed in the pad 222 after forming the pad 222 according the process described above. Alternatively, the openings 228 can be formed therein at any step in the manufacturing process.

Although the various embodiments have been described with reference to preferred implementations, persons skilled in the art will recognize that changes may be made in form and detail without departing from the spirit and scope thereof.

What is claimed is:

1. A fan-like cortical electrode device comprising at least two separate electrode segments, wherein each of the at least two electrode segments comprises:
   (a) a thin film pad, the thin film pad being a substantially triangular shaped thin film pad having a first width at a distal end of the thin film pad that is greater than a second width at the proximal end of the thin film pad;
   (b) a plurality of electrode contacts disposed on the thin film pad; and
   (c) a proximal connector attached to a proximal end of the thin film pad,
   wherein the at least two separate electrode segments are configured to be delivered separately such that a first outer edge of the thin film pad of each of the at least two electrodes segments is disposed adjacent to a second outer edge of the thin film pad of at least one other of the at least two electrode segments to form a fanned arrangement, and the proximal connectors of all of the at least two electrode segments are configured to be stacked together in a stacked configuration following delivery of each of the separate electrode segments such that the proximal connector of each of the at least two electrode segments is configured to be disposed through a single opening in a skull of a patient.

2. The fan-like cortical electrode device of claim 1, wherein each of the at least two electrode segments are nestable in deployment such that an outer edge of the fanned arrangement formed by the at least two electrode segments form a portion of a circle in which the plurality of electrode contacts are uniformly disposed across a surface of a brain of the patient.

3. The fan-like cortical electrode device of claim 2, wherein each of the at least two electrode segments are nestable in deployment such that the portion of the circle formed by the at least two electrode segments is a sector of the circle forming at least a half circle.

4. The fan-like cortical electrode device of claim 2, wherein each of the at least two electrode segments are nestable in deployment such that the at least two electrode segments form a full circle.

5. The fan-like cortical electrode device of claim 1, wherein the thin film pad comprises a first thin film layer, a second thin film layer, and a plurality of openings defined in the first thin film layer, wherein the plurality of electrode contacts are disposed between the first and second thin film layers such that each of the plurality of electrode contacts is accessible via one of the plurality of openings.

6. The fan-like cortical electrode device of claim 1, wherein the thin film pad comprises rounded corners.

7. The fan-like cortical electrode device of claim 1, wherein the thin film pad comprises at least one suture opening defined therein.

8. A fan-like cortical electrode system comprising at least two separate electrode segments, wherein each of the at least two electrode segments comprises:
   (a) a thin film pad having a substantially triangular shape, the thin film pad having a first width at a distal end of the thin film pad that is greater than a second width at a proximal end of the thin film pad;
   (b) a plurality of electrode contacts disposed on the thin film pad; and
   (c) a proximal connector attached to the proximal end of the thin film pad,
   wherein each of the at least two electrode segments is deployable separately from each other of the at least two electrode segments and positionable in relation to each other such that the thin film pad of each of the at least two electrodes segments is disposed adjacent to each other in a fanned arrangement to provide maximal coverage of a patient's brain.

9. The fan-like cortical electrode system of claim 8, wherein each of the at least two electrode segments are nestable in deployment such that the at least two electrode segments form a portion of a circle in which the plurality of electrode contacts are optimally disposed across a surface of a brain of the patient.

10. The fan-like cortical electrode system of claim 9, wherein each of the at least two electrode segments are nestable in deployment such that the at least two electrode segments form at least a half circle.

11. The fan-like cortical electrode system of claim 9, wherein each of the at least two electrode segments are nestable in deployment such that the at least two electrode segments form a full circle.

12. The fan-like cortical electrode system of claim 8, wherein the thin film pad comprises a first thin film layer, a second thin film layer, and a plurality of openings defined within the first thin film layer, wherein the plurality of electrode contacts are disposed between the first and second thin film layers such that each of the plurality of electrode contacts is accessible via one of the plurality of openings.

13. The fan-like cortical electrode system of claim 8, wherein the thin film pad of each of the at least two electrode segments comprises rounded corners.

14. The fan-like cortical electrode system of claim 8, wherein the thin film pad of each of the at least two electrode segments comprises at least one suture opening defined therein.

15. A fan-like cortical electrode system comprising at least two separate electrode segments, wherein each of the at least two electrode segments comprises:
(a) a substantially triangle-shaped thin film pad, the thin film pad being wider at a distal end of the thin film pad than at a proximal end of the thin film pad;
(b) a plurality of electrode contacts disposed on the thin film pad; and
(c) a proximal connector attached to the proximal end of the thin film pad,
wherein each of the at least two electrode segments is deployable separately from each other of the at least two electrode segments and positionable in relation to each other such that the thin film pad of each of the at least two electrode segments is disposed adjacent to each other in a fanned arrangement,
wherein the proximal connector of each of the at least two electrode segments is disposed in a stacked configuration upon deployment such that the proximal connector of each of the at least two electrode segments can be disposed through a single opening in a skull of the patient.

16. The fan-like cortical electrode system of claim 15, wherein each of the at least two electrode segments are nestable in deployment such that the at least two electrode segments form at least a portion of a circle in which the plurality of electrode contacts are optimally disposed across a surface of a brain of the patient.

17. The fan-like cortical electrode system of claim 15, wherein the thin film pad of each of the at least two electrode segments comprises at least one suture opening defined therein.

* * * * *